(12) United States Patent
Eriksson et al.

(10) Patent No.: US 10,830,759 B2
(45) Date of Patent: Nov. 10, 2020

(54) ARRANGEMENT FOR COLLECTION AND SEPARATION OF A BODY FLUID FOR PURPOSES OF ANALYSIS AND A METHOD RELATING THERETO

(71) Applicant: HEMCHECK SWEDEN AKTIEBOLAG, Karlstad (SE)

(72) Inventors: Bjorn Eriksson, Kristinehamn (SE); Annelie Brolinson, Karlstad (SE)

(73) Assignee: HEMCHECK SWEDEN AKTIEBOLAG (SE)

( * ) Notice: Subject to any disclaimer, the term of this patent is extended or adjusted under 35 U.S.C. 154(b) by 35 days.

(21) Appl. No.: 16/072,898

(22) PCT Filed: Jan. 26, 2017

(86) PCT No.: PCT/EP2017/051590
§ 371 (c)(1),
(2) Date: Jul. 26, 2018

(87) PCT Pub. No.: WO2017/133953
PCT Pub. Date: Aug. 10, 2017

(65) Prior Publication Data
US 2019/0072539 A1   Mar. 7, 2019

(30) Foreign Application Priority Data
Feb. 3, 2016   (SE) ...................... 1650130

(51) Int. Cl.
*G01N 33/49* (2006.01)
*A61B 5/15* (2006.01)

(52) U.S. Cl.
CPC ............. *G01N 33/491* (2013.01); *A61B 5/15* (2013.01); *A61B 5/150755* (2013.01)

(58) Field of Classification Search
None
See application file for complete search history.

(56) References Cited

U.S. PATENT DOCUMENTS 5,296,192 A   3/1994   Carroll et al.
5,846,837 A   12/1998  Thym et al.

FOREIGN PATENT DOCUMENTS

DE   2655977   6/1978
EP   0212634   3/1987
(Continued)

OTHER PUBLICATIONS

Patent Cooperation Treaty (PCT), International Search Report and Written Opinion for Application PCT/EP2017/051590 filed , dated Jan. 26, 2017, International Searching Authority, EP.

*Primary Examiner* — Richard C Gurtowski
(74) *Attorney, Agent, or Firm* — McDonald Hopkins LLC

(57) ABSTRACT

The present invention relates to an arrangement for collection and separation of a body fluid, e.g. whole blood, for purposes of analysis of a component, e.g. plasma, of a sample of the body fluid. It comprises means for receiving a body fluid, a filter arrangement (50) comprising a separation filter arrangement for separation of the component(s) to be analysed and a detection filter in communication with the separation filter arrangement. The filter arrangement comprises a pre-filter (6) having a filter volume adapted to be capable to receive a volume of body fluid exceeding a volume of a sample to be analysed, which comprises a first portion defining a sample zone volume arranged to form a sample zone and at least one second portion defining an excess removal zone volume, forming an excess fluid removal zone the volume of which exceeds said sample zone volume. The separation arrangement defines a separation zone volume, and flow control means (11A, 11A, 11B) are provided to control the transportation or flow of body fluid to the separation arrangement forming the separation zone and to the excess fluid removal zone.

17 Claims, 6 Drawing Sheets

(56) References Cited

FOREIGN PATENT DOCUMENTS

| | | |
|---|---|---|
| JP | H02141664 | 5/1990 |
| WO | 2013085462 | 12/2012 |

ARRANGEMENT FOR COLLECTION AND SEPARATION OF A BODY FLUID FOR PURPOSES OF ANALYSIS AND A METHOD RELATING THERETO

CROSS-REFERENCE TO RELATED APPLICATION

This application is a 35 U.S.C. § 371 national stage filing of PCT Application No. PCT/EP2017/051590 filed on Jan. 26, 2017, entitled "AN ARRANGEMENT FOR COLLECTION AND SEPARATION OF A BODY FLUID FOR PURPOSES OF ANALYSIS AND A METHOD RELATING THERETO," which claims priority to Sweden Patent Application No. 1650130-6, filed Feb. 3, 2016, each of which are incorporated herein in their entirety by reference.

TECHNICAL FIELD

The present invention relates to an arrangement for collection and separation of a body fluid for analysis, particularly, but not exclusively, for separation of plasma from whole blood in a sample, having the features of the first part of claim 1.

The invention also relates to a method for separation of a body fluid for analysis, particularly, but not exclusively, for separation of plasma from whole blood in a sample.

BACKGROUND

The use of body fluids for laboratory testing is a clinical routine which is extremely common and important within medical care. Different body fluids such as blood, cerebral spinal fluid and urine are used for different analyses. Body fluid tests are extremely important as diagnostic and prognostic tools, and particularly blood tests are extremely common.

Laboratory testing can generally be divided into three different phases, namely a pre-analytic phase, an analytic phase and a post-analytic phase. The pre-analytic phase can be said to comprise all steps taken before the actual analysis of a sample including patient variables, collection, handling and processing. The analytic phase comprises the analytic procedure, and the post-analytic phase comprises evaluation, documentation and reporting of variables.

It is of course of utmost importance that all the steps are performed in a correct manner in order to provide useful and reliable results allowing and giving appropriate guidance for the correct measures to be taken.

It is well known that a large amount, if not the majority, of errors in laboratory testing occur during the pre-analytic phase.

As far as blood testing is concerned, haemolysis is a current reason for rejection of a test sample, affecting the reliability and the accuracy in laboratory testing. Briefly, haemolysis is the release of haemoglobin and other intracellular components from erythrocytes to surrounding blood plasma as a consequence of damage or disruption of the cell membrane. Haemolysis may occur in-vivo as well as in vitro.

Haemolysis may particularly interfere with several biochemical analyses due to haemoglobin interfering with measurements, e.g. using spectrophotometric methods, and due to release of biochemical markers from broken red blood cells, in turn leading to false high values of such markers.

Visible haemolysis indicating a more generalized process of cell damage, generally cannot be observed until the separation of serum or plasma has occurred. Visible haemolysis is commonly defined as an extracellular haemoglobin concentration of above 0.3 g/L (0.0186 mmol/L), which results in a detectable pink-to-red hue of serum or plasma.

Detection of haemolysis is difficult, and is often associated with a time delay, particularly if separation of red blood cells from plasma or serum in collected blood samples is done e.g. by means of centrifugation in dedicated localities distant from the patient. In many modern laboratories an objective assessment is undertaken to determine the degree of haemolysis in every blood sample coming in for analysis. If the haemolysis is considered to be substantial enough to cause clinically relevant interference to the analysis, a new sample has to be collected from the patient.

Several problems are associated with the separation procedure, e.g. separation of plasma from whole blood for analysis and particular problems are due to the difficulties residing in the requirements that the correct amount of blood is provided to a separating arrangement for purposes of analysis, e.g. to allow for detection of haemolysis or any other analysis. In known arrangements, the amount of blood provided to the separating arrangement is extremely critical.

If the amount of blood is too large, the separation procedure may be ruined. Filter arrangements used in known devices for separation are not capable of handling excess blood, which thus may flow into the analysis area. If, on the other hand, the amount of blood is not sufficient, it will not be possible to obtain enough plasma for the analysis.

It is however extremely difficult to control the amount of blood provided to a collecting and separation arrangement. Manual steps are required and it is not possible to automatically control the amount of blood provided.

In known arrangements, attempts are done to improve the plasma yield during the separation procedure. This is however not satisfactory for several reasons, first the collected volume in itself is still extremely critical, and, if it is attempted to minimize the collected blood volume, the result may be that an insufficient amount of plasma is obtained in the separation procedure, meaning that a new sample has to be taken, or that results obtained in a subsequent analysis are unreliable. If it is desired to improve the separation with respect to parameters such as speed of filtration and/or possibly haematocrit level, with a given obtained amount of plasma, the separation yield has to be improved.

WO2013/085462 discloses a device for detection of haemolysis in a whole blood sample from a pierceable container comprising a transfer passage to a visible detection member in the form of a filter and means permitting transfer of a volume of plasma from the sample to the detection member via the transfer passage arranged through the container to the interior of said container for accessing the whole blood, a separation device for separating plasma from blood cells before the plasma reaches the detection member, and means providing a capillary action for urging the volume of plasma to be transferred through the separation device to the detection filter.

Through this arrangement, detection of haemolysis is considerably facilitated, but it is still very difficult to control the volume of the collected blood, which is very critical.

SUMMARY

It is therefore an object of the present invention to provide an arrangement for collection and separation of a body fluid for analysis as initially referred to through which one or more of the above-mentioned problems can be overcome.

Particularly it is an object of the present invention to provide an arrangement allowing a fast separation of a body fluid.

A particular object is to provide an arrangement for collection of and separation of a body fluid which is less sensitive to the amount of collected body fluid, particularly whole blood, than known arrangements.

It is also an object to provide an arrangement facilitating and speeding up collection and separation of e.g. whole blood for purposes of analysis, particularly, but of course not exclusively, for the purposes of quickly detecting haemolysis. It is thereby most particularly an object to provide a rapid way of detecting haemolysis in a whole blood sample, wherein an assessment preferably can be made within one minute, preferably within less than 30 seconds from initiating use of an arrangement according to the invention.

Another particular object is to provide an arrangement which allows for separation of blood containing more blood cells, higher haematocrit, than hitherto known arrangements.

A most particular object is to provide an arrangement which is easy and cheap to fabricate, in particular a disposable arrangement.

In particular, it is also an object of the present invention to provide an arrangement which is easy to use and operate and reliable independently of initially collected body fluid volume.

Still further it is an object to provide an arrangement which is reliable and precise in operation.

Another most particular object of the invention to provide an improved way of assessing haemolysis in immediate connection to collecting a blood sample, said assessment being possible to perform by a user e.g. in a treatment room without the necessity of a laboratory, even more particularly allowing the user collecting a blood sample to perform the steps for detecting haemolysis by using one hand only. A "user" here refers to any person operating the arrangement for performing an analysis, e.g. detecting haemolysis, and may include e.g. a medical practitioner, a health care provider and/or laboratory staff or a veterinarian.

It is also a particular object of the invention to provide a way of assessing haemolysis using only a very small volume whole blood sample, preferably between 20-200 μl whole blood, preferably resulting in between 1-50 μl plasma volume for detection.

Therefore an arrangement as initially referred to is provided which has the characterizing features of claim 1.

It is also an object of the present invention to provide a method as initially referred to through which one or more of the above mentioned problems can be solved.

Advantageous embodiments are given by the respective appended dependent claims.

It is a particular advantage of the invention that a fast separation is enabled. It is also a particular advantage that an arrangement and a method respectively is provided which has a low sensitivity to variation in initial blood volume. Still further it is an advantage that separation of blood with more blood cells, a higher hematocrit, is enabled.

According to the present invention it is not aimed at increasing the yield, but instead it has been realized that, through increasing the initial volume of blood, the desired plasma volume can be obtained using an arrangement as described.

The skilled person understands that the term "body fluid" encompasses various types of fluids to be analysed, for example (but not limited to) whole blood, cerebral spinal fluid and urine.

BRIEF DESCRIPTION OF THE DRAWINGS

The invention will in the following be further described in a non-limiting manner, and with reference to the accompanying drawings, in which.

DETAILED DESCRIPTION

Figure 1:
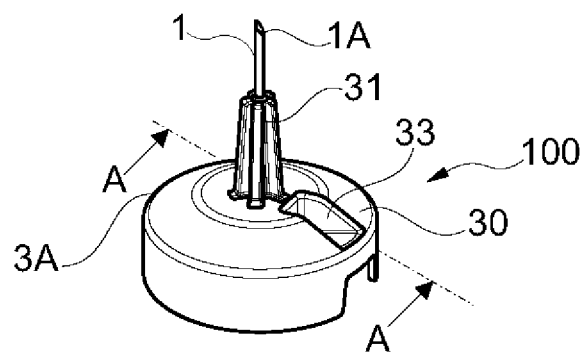
FIG. 1 is a view in perspective of an arrangement according to one embodiment of the invention.

FIG. 1 is a schematic view in perspective of an arrangement 100 for collection and separation of a body fluid, most particularly whole blood, for analysis. One end of the arrangement 100 is provided with a needle element 1 or similar, which, when not in use, preferably is provided with a protective element, e.g. a cap or similar of rubber, plastic or similar (not shown). The needle element 1 has an outer end tip 1A adapted to be introduced through a sealing member of e.g. a stoppered container or similar (not shown) containing the body fluid, e.g. whole blood. A "blood collection arrangement" here may be taken to include (in a non-limiting sense) a stoppered container, a collection tube, a blood collection tube, a conventional tube, a blood bag and a capillary tube. A test tube may refer to a stoppered tube, a collection tube, a blood collection tube, a conventional tube and vice versa. Further, a "stoppered tube" refers to a, normally airtight, container of glass, plastic or similar, arranged to contain a volume of liquid biological specimen therein, e.g. a whole blood sample. Normally, such stoppered tubes are provided with an open end having a pierceable stopper or sealing member (of rubber or the like) positioned in the open end. Such a construction is typical for closed specimen tubes which are manufactured under reduced atmospheric pressure, losing all or most of their vacuum when being filled. The needle is held within a dispensing body 31 e.g. comprising a substantially annular abutment member, and further comprising a surface adapted to engage with the container or similar containing the whole blood.

In particular embodiments, to which the inventive concept however is not limited, the dispensing body 31 limits the length of the needle 1 that can penetrate the sealing member of the container, which length however is sufficient to allow penetration of the sealing member and entering an additional distance into a well space immediately adjacent to an inner surface of the sealing member in order to get into contact with the body fluid sample (particularly whole blood) disposed therein.

The diameter of the dispensing member 31 particularly may be smaller than an average concave diameter of a sealing member concave depression and the dispensing member 31 is also longer than the maximum depth of the concave depression of the sealing member so that the dispensing member 31 is always operative to effect a flexing or distortion of the sealing member e.g. forcing it inwardly towards a centre of the container. The needle element 1 extends through the dispensing member 31 into a housing 30 arrangement comprising a housing outer, or top, part 3A and a housing inner, or bottom, part 3B. The other outer end portion of the needle, opposite to the first outer end portion 1A, ends at a slight distance from a filter arrangement 50 (see FIG. 2) as will be more thoroughly described below. Reference numeral 33 schematically illustrates an exemplary portion of the outer housing 3A internally providing a shoulder, which portion however is not of any relevance for the functioning of the present invention, and may just as well be disposed of.

A transfer channel is hence formed by the passage from the needle tip 1A and the needle end portion ending in the housing 30, allowing passage of blood from the container (not shown) to the filter arrangement 50 as will be further discussed below.

It should however be clear that the present invention is not limited to receiving a sample by means of a needle element and a container, on the contrary, it also covers other manners of receiving a sample, by means of a pipette, a syringe or manually etc.

Figure 2:
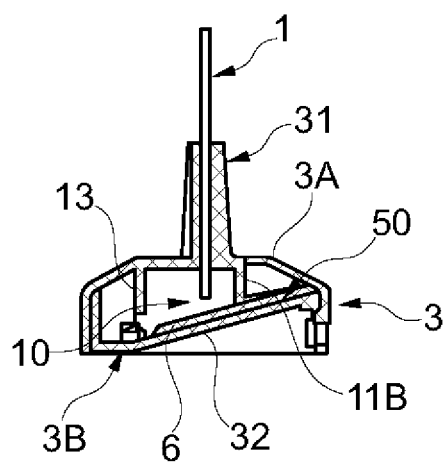
FIG. 2 is a view in cross-section taken along the line A-A in FIG. 1.

FIG. 2 is a cross-sectional view taken along the line indicated A-A in FIG. 1. As can be seen in FIG. 2, the needle element 1 extends through the dispensing member 31 into the interior of the housing arrangement 30 comprising a housing outer part 3A and a housing inner part 3B as referred to above, with its opposite outer end portion located at a slight distance from a filter arrangement 50 which is disposed on a bottom support portion or plane 32 of the housing inner part 3B.

The bottom support portion 32 is in the here illustrated embodiment arranged in an inclined, sloping manner, e.g. forming an angle of about 70°-80° with the longitudinal extension of the needle element, or 10°-20° with a bottom plane formed by the bottom portion of the housing arrangement 30. It should however be clear that the exemplified angular dimensions by no means are limitative. In other embodiments the angle may be larger as well as smaller. One reason for having a sloping bottom support portion 32 is that the part of the blood that is to be filtered, or separated, to plasma, might be transported by means of capillary action rather than by gravity.

In still other advantageous embodiments the bottom portion is not arranged in a sloping manner, but is planar, e.g. perpendicularly disposed with respect to the longitudinal extension of a needle 1 or a dispensing member.

The filter arrangement 50 comprises a pre-filter 6 as will be further discussed with reference to FIG. 6 and FIGS. 7A-7D in which some alternative embodiments of a pre-filter are shown, said pre-filter being disposed on top of a separation filter arrangement comprising one or more separation filters 5 (see FIG. 9) and a detection filter 7 (see FIG. 10), or a separation filter also comprising a detection zone, i.e. a separation filter serving both the purpose of separation and of providing a detection zone. How the filters may be arranged and disposed on the bottom support portion 32 of the housing inner part 3B according to one embodiment is illustrated in FIGS. 11A-11C.

The housing outer, or top, part 3A comprises an outer surrounding wall section arranged to surround an outer wall section of the housing inner part 3B. The arrangement further comprises flow controlling means arranged to control the flow of the blood as will be more thoroughly described below. In the shown embodiment the flow controlling means are formed by walls 11A, 11A, 11B, 11A', 11B', 11C' (11C' only in the embodiment shown in FIG. 7D) of a sampling chamber 10 (see also FIG. 3) of which walls, in FIG. 2, only wall 11B can be seen. Reference numeral 13 in FIG. 2 indicates a wall which merely is provided for stability and structural reasons, but otherwise does not play any role for the functioning of the present invention, which therefore of course is not limited to the provisioning of such a wall. The sampling chamber walls 11A, 11A, 11B are in the shown embodiment arranged to exert a pressure on the pre-filter 6 for controlling, particularly delaying, the flow from the central portion of pre-filter 6, forming a sample zone Z1, to the outer portions of the pre-filter, forming blood excess zones Z2.

The housing outer or top part 3A may be provided with protruding edges, e.g. provided with snap in members, to enable fixation to the housing inner or bottom part 3B by snap in. The housing inner or bottom part 3B may be provided with a peripheral (e.g. circular) edge that is adapted to fit into within said protruding edges of the housing outer or top part 3A. These features are not specifically indicated in FIG. 2 since releasable connection between the housing inner and outer parts may be provided for in many different manners.

It should further be clear that also embodiments where the outer periphery of the housing bottom part 3B is larger than the outer periphery of the housing top part 3A are possible. A snap in function or any other connection may be provided for releasable interconnection of the two housing parts.

Figure 3:
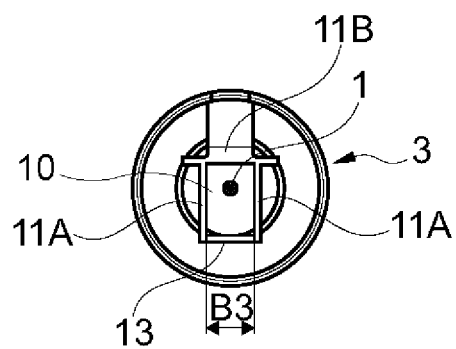
FIG. 3 is a cross-sectional view through the housing, taken from the above, of the arrangement in FIG. 1.

FIG. 3 is a view from below of the arrangement 100 showing the walls 11A, 11A, 11B forming the sampling chamber and acting as flow control, or flow delaying, means. The wall 11B may, but does not have to, be provided on a shoulder as mentioned above. The optional support wall 13 does not come into contact with the pre-filter 6. The outer wall of the housing outer, or top, part 3A in the shown embodiment is of a cylindrical shape and surrounds the outer wall of the housing inner, bottom, part 3B.

At its upper end, the outer wall of the housing outer or top part 3A tapers, and is arranged to take up the dispensing member 31. The walls 11A, 11A, 11B are arranged inside of said outer wall of the housing outer or top part 3A, in the shown embodiment at a substantially flat section in the tapering region, and form a sample chamber 10 of a rectangular cross-section (here) with one at least partly open side.

The width B3 of the sampling chamber 10 is in one embodiment ca 5.5 mm, although it of course may be larger as well as smaller, even considerably larger or smaller depending on application.

As also referred to above, the walls 11A, 11A, 11B define the sampling chamber 10 as will be more thoroughly discussed below, particularly with reference to FIG. 6, and which preferably, but not necessarily is open in one end, opposite to wall 11B.

Figure 4:
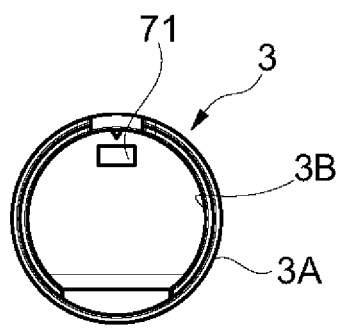
FIG. 4 is a view from below of the arrangement in FIG. 1.

FIG. 4 is a schematic view from below of the arrangement for collection and separation 100 showing the housing arrangement 30 with the outer surrounding wall section of the housing outer, or top, part 3A surrounding the outer wall section of the housing inner part 3B. In one embodiment the walls, i.e. the bottom wall and the side wall or walls of the housing inner, bottom, part 3B are made of a transparent plastic material. A label with a detection window 71 may be glued or otherwise attached to bottom support portion 32, such that only the detection filter e.g. is visible or otherwise recognizable from below for purposes of analysis, i.e. from the bottom of the arrangement 100, e.g. allowing for detection or assessment of haemolysis, or exclusion of the presence of haemolysis. If the bottom support portion 32 is not transparent, an opening is taken up to provide a detection window. Then no label is needed.

In advantageous embodiments also the housing outer part 3A is made of a plastic material which may be transparent or not.

Figure 5:
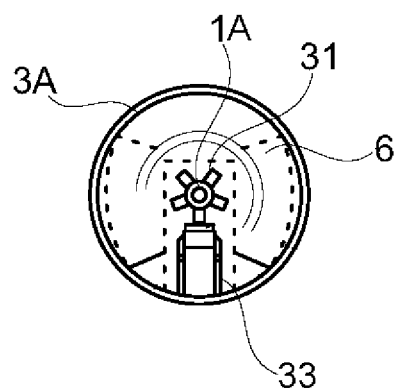
FIG. 5 is a schematic view taken from above of the upper part of the housing of the arrangement in FIG. 1.

FIG. 5 is a very schematic top view of the arrangement 100 of FIG. 1 showing the housing outer, top, part 3A, and the dispensing member 31. The pre-filter 6 is illustrated through dashed lines. The shoulder 33 forming recess is, as mentioned above, not necessary for the functioning of the invention. In other, not shown, embodiments, a detection zone might be arranged under such a recess, which hence has to be transparent. Further, the cross-sectional shape of the dispensing member 31 may of course be cylindrical or of any other shape, the flanges merely being provided for reasons of enhancing the stability of the arrangement.

The filter arrangement e.g. used for separation of plasma from whole blood for purposes of analysis will be further discussed and exemplified below.

According to the invention, instead of improving or enhancing the yield of plasma obtained by means of the separation, it is enabled that a desired volume of plasma is obtainable from a larger amount of initial blood volume, or in more general terms, body liquid volume.

Basically the inventive procedure carried out by means of the arrangement can be said to comprise two sub-procedures, which are separated in time as well as in space.

The blood separation is timely, by means of appropriate timing, divided into two sequential phases, namely a first phase in which blood is separated from plasma, and a second phase in which excess blood is removed.

Figure 6:
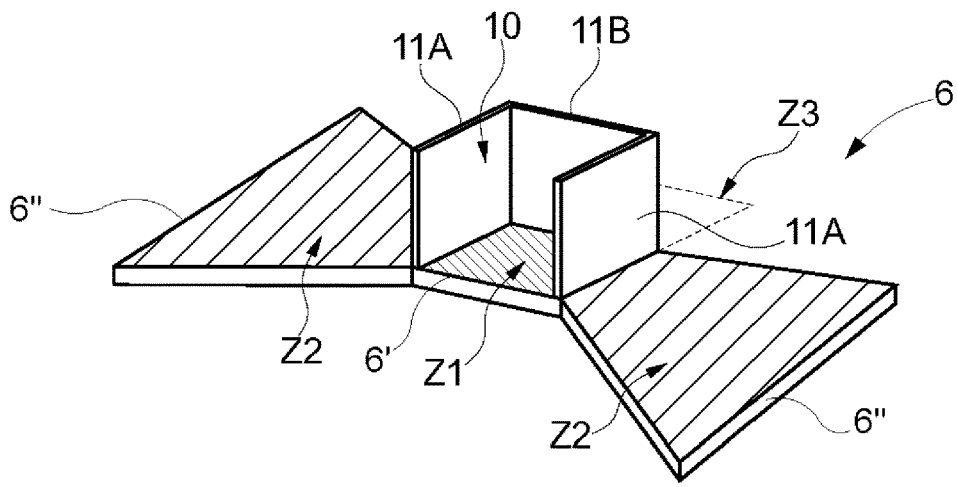
FIG. 6 is a view in perspective of an exemplary pre-filter and showing a sampling zone and a separation zone according to one embodiment.

In the first phase, an initial separation phase, a fraction of the blood sample, in a sampling zone Z1; cf. FIG. 6, is transported and separated into plasma to a desired area or zone, also called a separation zone Z3 associated with a detection area, see FIG. 6. It has been realized that, for the initial separation phase, it is advantageous to have an excess, or even a large excess, of blood at the starting point, and a filter allowing a fast transportation of plasma, but with a limited filter volume.

The inventive concept is particularly advantageous if used for setups where the separation phase is based on different transport velocities for blood and plasma respectively. In the first, initial, separation phase, the plasma should relatively fast fill the entire separation and detection filter volume, and the desired plasma be collected at the end of the flow path forming a so called dead end, e.g. separation zone Z3 in FIG. 6. Any extra volume holding filter after the collection of plasma would affect the separation in a negative manner. The separation zone may be horizontally or laterally disposed.

In the second phase, a blood excess removal phase, when the desired amount of plasma has been obtained, the initial large excess of blood is undesired and may lead to blood cells leaking into the plasma and the blood cells will eventually fill up the limited volume of the separation phase (in separation zone Z3) unless removed. Therefore a large volume filter (zones Z2, Z2; Z2 of the pre-filter) with a slower transport is used to assist in removing and storing the excess blood; see e.g. zones Z2, Z2 in FIG. 6.

The total volume of the pre-filter has to be large enough in order to not be completely filled with the largest intended blood volume, since if the blood completely fills up the filter, the blood will start filling up the separation path as well. The filter shall hence be so constituted and/or arranged that parts of it preferably in all cases remain thy.

Thus, the timing and the speed of the two phases are of utmost importance for a successful separation. If the second phase, the excess removal phase, is too fast in relation to the separation phase, not enough plasma, or even no plasma at all, will be separated and transported or flow to the separation zone Z3.

If, on the other hand, the excess removal phase is too slow in relation to the separation phase, the initial separation will be lost as the blood cells fill the separation path, and are transported to the separation zone Z3.

According to the invention, the speed, and the initiation, of the excess blood removal phase can be controlled in different manners.

In some advantageous embodiments, as will also be further explained below, mechanical control means are provided for controlling the excess blood removal speed (and initiation). One way of using mechanical control means is to arrange mechanical means capable of, in a predetermined, or in a controllable manner, apply a mechanical pressure to a large blood excess collecting filter (the pre-filter) to form tighter parts slowing down the blood transport through the pre-filter. A higher mechanical pressure gives a slower transport, as is also illustrated through FIGS. 8A,8B, whereas a lower, or no, mechanical pressure enables a faster transport.

Other means for controlling the phases, particularly the speed of the excess blood removal phase, are e.g. other means for creating a barrier, e.g. a hydrophobic coating acting as a barrier etc.

According to the present invention a filter arrangement is provided which enables a blood separation path having the properties of a fast liquid transport, good blood separation properties and a higher flow velocity of plasma than of blood cells, and a small filter volume. For the blood excess removal path, the filter arrangement has the properties of providing a slow liquid transport, a large filter volume, and no requirements on blood separation properties.

To provide a separation path and a blood excess removal path having the features discussed above an exemplary pre-filter 6 of a filter arrangement is disclosed in FIG. 6. Sections of exemplary filter arrangements, comprising a pre-filter, a separation filter arrangement and a detection filter are shown in FIGS. 11A, 11B.

FIG. 6 discloses a sample chamber 10 disposed on a pre-filter 6. Into the sample chamber 10, comprising two side walls 11A, 11A, as also described with reference to FIGS. 2,3,5, the fluid, here blood, is introduced from the top. The sample chamber 10 here comprises but three walls, which however is not necessary but advantageous, particularly in embodiments in which the chamber 10 is closed upwards, in order to allow air to escape on the side where there is no wall. If on the other hand, the construction is not closed upwards, e.g. if the body fluid is to be received by means of a pipette, a syringe or using a finger, the sample chamber may instead have four walls. Different constructional alternatives are possible.

The pre-filter 6 here comprises a first portion, e.g. of a square shaped or rectangular form, forming a sample zone Z1 which on three sides is limited by the walls 11A, 11A, 11B. Symmetrically with respect to the first portion, forming the sample zone Z1, two outwardly flaring wing portion 6" extend in opposite directions, forming a blood excess zone Z2, Z2. The wing portions 6",6" each have an area or volume exceeding that of the first, sample, portion 6'. In communication with the first portion forming the sample zone Z1 a separation zone Z3 is indicated through a dashed line and in which blood plasma is collected at the dead end of the flow path as discussed above.

The pre-filter filter 6 volume is thus divided into a sample zone volume and a blood excess volume, a filter volume being given by the filter area x filter thickness. The total filter volume of the pre-filter 6 needs to be such as to exceed the maximum volume of blood intended to be used, preferably with a margin. Hence, particularly the total area of the pre-filter should be such as to give a filter volume exceeding the maximum volume of the blood intended to be used. The excess blood zone volume depends on the used blood volume, but needs to be at least twice the sample zone volume, but in principle cannot be too large.

In advantageous embodiments the sample zone Z1 filter volume should be such that an initial blood volume is at least 1.5-10 times the sample zone Z1 filter volume, more particularly 2-4 times the sample zone Z1 filter volume. As an example given for illustrative purposes only, and by no means in a limitative sense, if initially a sample of 100 µl blood is used, the volume of the sample zone filter should be about 67 µl (or mm$^3$), which however also depends on the used separation system. For controlling or delaying the flow, in the shown embodiment, the walls 11A, 11A, 11B act as mechanical control means through exerting a mechanical pressure on the pre-filter 6 along the borders between the sample zone and the blood excess zone(s).

As discussed above, a large volume of blood in the sample zone Z1 is beneficial in the initial separation phase, but once the desired amount (volume) of plasma has been collected, a large blood volume becomes a problem and excess blood needs to be removed. If the excess blood in this stage is not removed from the sample zone, it may migrate into the detection zone, or the separation zone Z3, and the timing in removing excess blood from the sample zone Z1 is critical and essential for the separation.

In the shown embodiment the blood transport from the sample zone Z1 to the blood excess zone Z2, Z2 is controlled or delayed by means of the flow control or delay means 11A, 11A, 11B formed by the walls of the sample chamber 10 forming or acting as a barrier between the zones, providing a compression of the pre-filter 6 along the barrier forming a zone border. The walls 11A, 11A, 11B can hence be used to adjust the delay of the blood transport to the blood excess zone Z2, Z2 by compressing the pre-filter along the zone border, and the degree or amount of compression is used to acquire the accurate timing of the blood transport to the blood excess zone Z2, Z2.

Figure 8A:
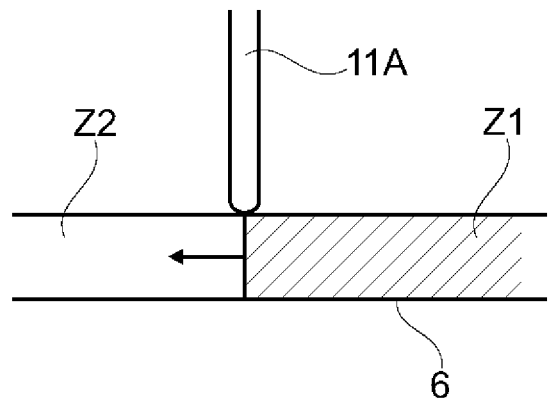

FIG. 8A very schematically illustrates a state of a wall of a sample chamber 11A acting as a mechanical control, by compression, means at the border between a sample zone Z1 and a blood excess zone Z2 in which a very low pressure is exerted on the pre-filter 6. If the pressure is too low, the transfer of excess blood to the blood excess zone Z2 may be too high, which may have as a consequence that no plasma is obtained.

Figure 8B:
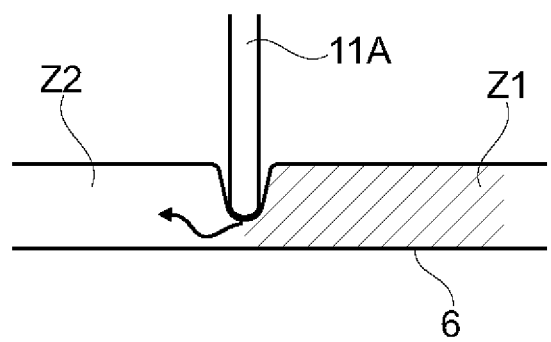

FIG. 8B illustrates a state in which instead a high pressure is exerted by the wall 11A on the pre-filter 6 along the border between the sample zone Z1 and the blood excess zone Z2. A high pressure slows down the transport of excess blood from the sample zone Z1. If the pressure is too high, blood may enter the separation zone, and hence into the collected, separated plasma.

In alternative embodiments a hydrophobic protecting device or coating between the sample zone and the blood excess zone(s) can be used instead as a flow control or delay means. In still other embodiments the first filter portion may comprise an extremely narrow filter passage, a narrow filter waist, forming a flow control means.

Figure 7A:
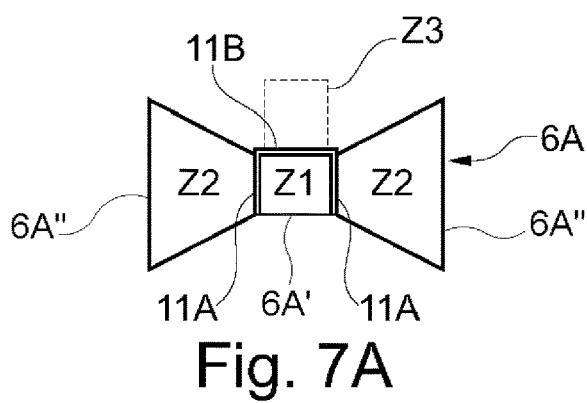
FIG. 7A is a top view of a pre-filter according to one embodiment.
Figure 7B:
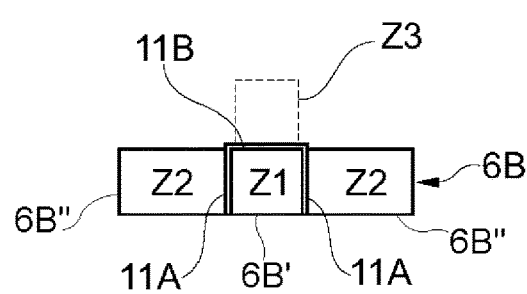
FIG. 7B is a top view of a pre-filter according to another embodiment.
Figure 7C:
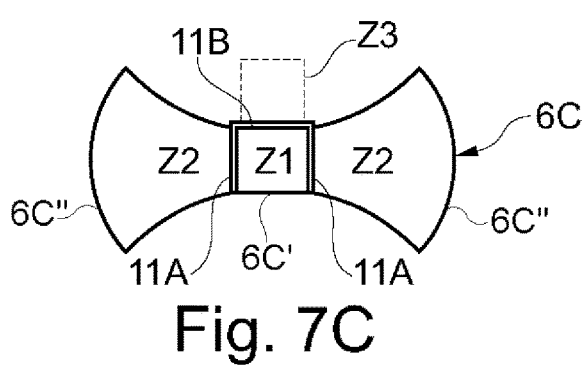
FIG. 7C is a top view of a pre-filter according to a third embodiment.
Figure 7D:
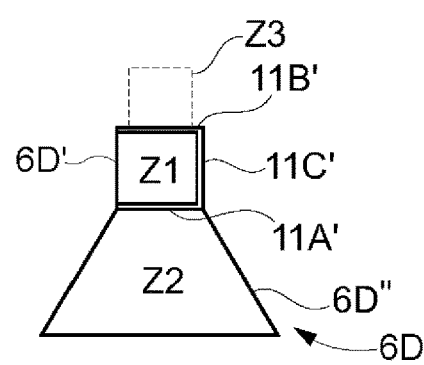
FIG. 7D is a top view of a pre-filter according to a fourth embodiment, FIG. 8A schematically illustrates a volume controlling arrangement arranged to act on a pre-filter in one state, FIG. 8B schematically illustrates the volume controlling arrangement arranged to act on the pre-filter in another state, FIG. 9 schematically illustrates an exemplary separation filter, FIG. 10 schematically illustrates an exemplary detection filter.

FIGS. 7A-7D shows some different embodiments of pre-filters 6A, 6B, 6C, 6D. Similar elements bear the same reference numerals as corresponding elements in FIG. 6 and will not be further discussed herein. Generally an efficient transportation of blood into the excess zone(s) Z2, Z2; two zones respectively, one on either sides of the sample zone Z1 in the embodiments of FIGS. 7A-7D, and one excess zone Z2 in the embodiment of FIG. 7D, is needed, which can be provided for in different manners as discussed above. The shape of the pre-filter can also be adapted to different types and sizes of housings.

If a lateral/horizontal separation is utilized, the blood excess zone(s) Z2, Z2; Z2 is/are to be located in a different direction than the separation zone Z3, or the separation zone and the detection zone. If the area(s) of the pre-filter forming the blood excess zone(s) Z2, Z2; Z2 increases further away from the sample zone Z1, e.g. is cone shaped, cf. FIGS. 7A, 7B, 7D, an accelerating transportation of excess blood is provided when blood is removed from the sample zone Z1, which is extremely advantageous. This is however not necessary; in alternative embodiments the width of the pre-filter 6B is substantially the same close to the sample zone Z1 as at the outer end of the blood excess removal zone Z2, Z2. The lack of an accelerating transport may then e.g. be at least compensated for by exerting a somewhat lower pressure by means of the walls 11A,11A as compared to the pressure exerted in an embodiment in which the pre-filter is larger further away from the sample zone Z1. In all embodiments, in case of upwardly closed sample chambers, there is preferably no barrier or wall at a side not forming a border between different zones, e.g. in FIGS. 7A-7C on the side facing away from the separation zone Z3.

In the embodiment shown in FIG. 7D the blood excess zone Z2 of the pre-filter 6D only extends on one side of the sample zone Z1, on a side opposite to the side at which the separation zone Z3 is located, the zone borders, where the control means formed by the sample chamber walls 11A', 11B' being located between the sample zone Z1 and the separation zone Z3 and the blood excess zone Z2 respectively. The sample chamber walls 11A',11B' are here interconnected by means of an optional rear wall 11C'.

As should be clear from the above, the pre-filter may have many different shapes. It is of course also possible to have four walls forming a sample chamber, with an opening in one of the walls, in a direction where there is no blood excess zone, in order, i.e. to allow air to escape, to let air out when blood is let in.

The pre-filter 6 in advantageous embodiments is made of a porous, hydrophilic material. In particular embodiments it is made of glass fibre. It should be clear that the dimensions may vary a lot from one embodiment to another and for different applications, different types of filters etc. As an example only, the pre-filter 6C shown in FIG. 7C may have a total length of about between 15-25 mm, e.g. 18-20 mm and a narrowest width in the sample zone, of about 6-10 mm, e.g. about 8 mm. It may e.g. have a thickness of about 0.5-0.9 mm, e.g. about 0.7 mm. It should of course be clear that the dimension ranges exclusively are given for exemplifying reasons, and hence by no means for limiting purposes.

The separation zone Z3 is formed by a separation filter arrangement, which may comprise one or more separation filters, as also can be seen from FIGS. 6,7A-7D, and the separation zone Z3 is in contact with the sample zone Z1 of the pre-filter 6; 6A; 6B; 6C; 6D as will be more thoroughly described with reference to FIGS. 11A-11C. The separation mechanism is generally based on the different transport velocities of the plasma and of the blood cells. Advantageously the plasma is collected for analysis at the "dead end" of the transport direction as also mentioned above. The total volume of the separation filter arrangement is preferably smaller than that of the sample zone filter volume.

Figure 9:
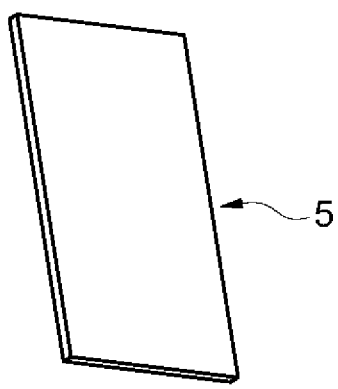

FIG. 9 shows in a very schematic manner a separation filter 5. As referred to above, the separation filter arrangement may comprise one or more separation filters, e.g. 1, 2, 3 or 4 separation filters or even more. They may be of different shapes, sizes and thicknesses.

In one embodiment the separation filter arrangement comprises a first separation filter 5 wherein e.g. the separation filter 5 is located at least partly below another separation filter, or vice versa. If there are more than one separation filter in a separation filter arrangement, they may have the same size, shape, and thickness, or one or more of the parameters may be different.

The separation filter 5 may e.g. have dimensions in the order of 3-5 mm×6-9 mm, in the shown embodiment ca. 3.6×8.3 mm and a thickness of about 0.25 mm. It should be clear that the dimension ranges exclusively are given for exemplifying reasons, and hence by no means for limiting purposes.

The separation arrangement hence comprises one or more separation filters (or separation membranes) arranged to separate plasma from the cellular components of whole blood sample without lysis. The filter may be any known conventional filter or membrane which meets the separation requirements of the present arrangement, including membranes made from synthetic and natural polymers, preferably, but not necessarily, a hydrophilic membrane. According to one embodiment the separation filter is asymmetric meaning the filter pores have varying sizes. The filter may have any suitable geometry or shape, e.g. being substantially flat or being three dimensional, e.g. cylinder shaped. The size and/or volume of the filter(s) depends on the filter type as well as the specific plasma volume that is to be separated there through.

Figure 10:
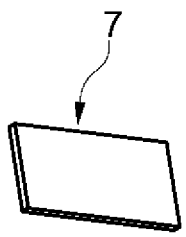
Figure 11A:
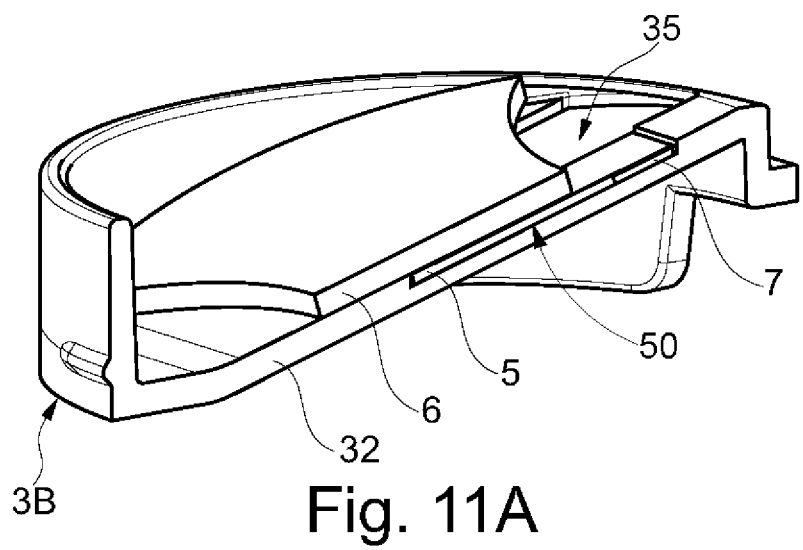
FIG. 11A is a schematic view in cross-section of a filter arrangement arranged in a housing.
Figure 11B:
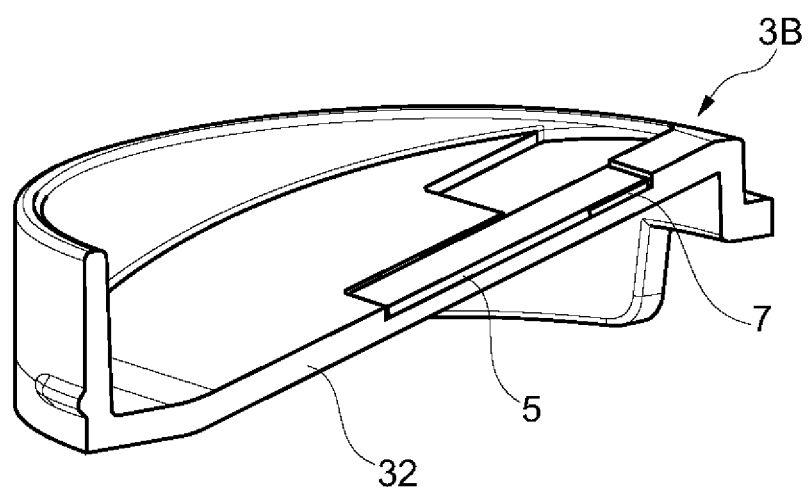
FIG. 11B is a schematic view in cross-section of the filter arrangement of FIG. 11A with the pre-filter removed for illustrative purposes.
Figure 11C:
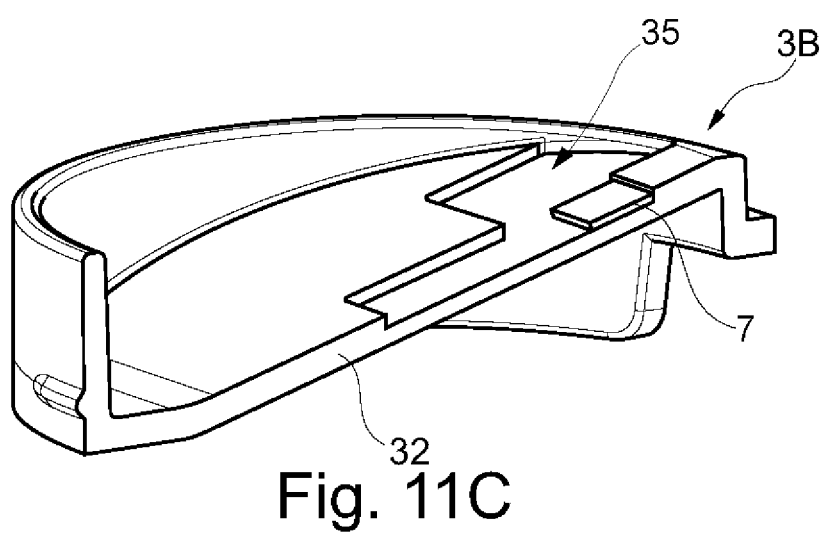
FIG. 11C is a schematic view in cross-section of the filter arrangement of FIG. 11A with the pre-filter and the separation filter removed for illustrative purposes.

FIG. 10 is a very schematic view of an exemplary detection filter 7 adapted to be arranged adjacent to, and substantially in the same plane as the separation filter, in a plane below the pre-filter, but outside the sample zone (see FIGS. 11A-11C). Exemplary dimensions of the detection filter 7 are in the range of 1.8-2.5 mm×3-4.2 mm, with a thickness of about 0.1-1.0 mm, particularly about 0.2-0.3 mm. It may e.g. be made of cellulose or glass fibre. Alternatively it may comprise a filter made of a porous material, e.g. having a thickness of about 0.1-5 mm. Also here it should be clear that the dimension ranges exclusively are given merely for exemplifying reasons, and hence by no means for limiting purposes.

The detection filter may e.g. be made of any suitable material which provides a capillary action and fulfils other requirements of the present invention, such as a cellulose or glass fibre material, a woven filter or a non-woven filter or even certain cloth materials.

In still other advantageous embodiments there is no separate detection filter, but the separation filter is adapted to provide also a detection zone, substantially located as the detection filter shown in FIGS. 11A-11C. Thus, the separation filter comprises a detection zone which is the zone where the separated plasma is collected. In the following, when referring to a detection filter or a detection zone, this may comprise a zone on the separation filter or a zone formed by a separate detection filter.

A capillary action, or capillarity, here means the ability of a liquid to flow against gravity where the liquid spontaneously rises in a narrow space such as in a porous material like paper or a filter. Through the capillary force an efficient plasma separation is obtained through a separation member (the separation filter) and provides a reliable transfer of the resulting plasma sample into the detection zone, no additional external force being required for acquiring said transfer, whereupon assessment of plasma hue may be performed through the window 71 in the label on the bottom side of the bottom support surface 32.

For visually inspecting the detection zone 7 and the plasma therein to determine whether or not haemolysis has occurred in the blood sample, it is e.g. possible to use a chemical agent comprising a colour reagent in the detection zone, e.g. the detection filter, which changes colour if there is haemoglobin in the plasma, haemolysis has occurred. This enables a particularly safe and reliable test result and an easy evaluation. A common method for colorimetric detection of haemoglobin is Drabkin's reagent, which consists of potassium cyanide. Other alkali cyanides as well as ferricyanides could also be used. Further examples of chemical means facilitating visual detection may include colorimetric methods making use of the peroxidase activity of haemoglobin, based on a chromogen such as benzidine compounds with peroxides as substrate. The colour reagents may be deposited inside the detection zone 7 either in dried form or as a wet reagent, or as a combination of dry and wet reagents.

If haemolysis is suspected, the blood sample should be replaced.

If no haemolysis is detected, the arrangement 100 can discarded as waste material, and a tube or similar with the sample can be used for further analysis.

In order to facilitate assessment of haemolysis, the arrangement may be provided with a colour reference for comparison with the sample plasma, e.g. showing a cut-off colour, and if the plasma colour is different from, e.g. darker than, the reference, haemolysis can be suspected and vice versa. Such colour reference may e.g. be provided next to the visible detection zone 7.

Thus the visual detection allows substantially a direct visual detection providing a result almost instantly.

In some embodiments the separation filter arrangement 5 comprises a separation filter (or separation membrane) arranged to separate plasma from the cellular components of whole blood sample without lysis. The filter arrangement may comprise any known conventional filter or membrane which meets the separation requirements of the present equipment, including membranes made from synthetic as well as natural polymers, preferably, but not necessarily a hydrophilic membrane. According to one embodiment the separation filter is asymmetric meaning the filter pores have varying sizes. The filter may have any suitable geometry or shape, e.g. being substantially flat or three dimensional, e.g. cylinder shaped. The size and/or volume of the filter depend on the filter type as well as the specific plasma volume that is to be separated there through.

In advantageous embodiments the separation filter and the detection filter comprise a porous structure generating a capillary action whereby plasma is urged to pass through both of the respective filters. The visual examination of plasma hue is performed the moment plasma has been drawn into the detection zone to such an extent that the plasma is visible through e.g. the detection window. The detection zone may comprise only the detection filter which may be covered by a transparent label or cover as discussed above through which the interior of the detection zone, or the detection filter, may be observed. It should be clear that the detection zone and the detection window may be arranged elsewhere in the arrangement, e.g. on the housing top portion 3A, as long as the filters of the filter arrangement and the control means are arranged such that the functionality described above with reference to the exemplary embodiments is achieved.

Once a volume of blood is applied onto the separation filter it, will be drawn into the structure of the separation filter arrangement directly upon exiting the transfer passage (e.g. a needle) thanks to capillary action, whereby the plasma is separated from the red blood cells. The adjacently arranged detection filter, or the part of the separation filter forming the detection zone, in turn is arranged to also provide a capillary action, and the volume of plasma, when having passed the separation zone, will continue to be drawn into the detection zone to such an extent that it becomes visible on the opposite side of the detection zone, e.g. the detection filter, as the plasma is transferred there through.

Since haemolysis is visually detectable in serum or plasma, it becomes possible for a user to, immediately, visually determine if a clinically significant haemolysis is present in the sample, e.g. before a tube or similar containing the sample is sent to a laboratory for further analysis. This may be done by merely observing the hue of the plasma portion having been absorbed by the visible detection zone filter.

The detection filter may in alternative embodiments be in the form of a porous material such as glass wool which also provides the desired capillary action allowing separated plasma to be sucked up to such an extent that the detection filter is coloured by the hue of the plasma whereby assessment of haemolysis in the blood sample may be determined visually.

FIG. 11A is a sectional view through the housing inner, bottom, part 3B comprising a bottom support portion or plane 32 on which the filter arrangement 50 is disposed. The bottom support plane here 32 is arranged in a sloping manner with an inclination as discussed above with reference to FIG. 3. The filter arrangement 50 comprising a pre-filter 6, a separation filter arrangement 5 and a detection filter 7 is shown. On the top, the pre-filter 6 is disposed, the section being taken through the narrower portion of the pre-filter forming the sample zone. Below the pre-filter 6 the separation filter arrangement, here comprising but one separation filter 5, is disposed in a recess 35 in the bottom support plane 32. The separation filter 5 is disposed under the portion of the pre-filter 6 forming the sampling zone, and on one side, the upper side of the sloping bottom plane 32, protruding beyond the narrow portion of the pre-filter 6. Next to the protruding portion of the separation filter 5 the detection filter 7 is disposed, also taken up in the recess 35 in the bottom support plane 32.

It should be clear that, as also mentioned earlier, the bottom support plane 32 does not have to be arranged in a sloping manner, but may just as well be arranged in a planar manner, i.e. disposed to form zero sloping or inclination angle with a horizontal plane formed by lower outer ends, or the outer wall, of the housing inner, bottom, part 3B. Alternatively there may be any other inclination angle.

One reason for having the inclination is that it might improve the functionality of the arrangement in some situations where there may be a risk that an overfill of blood may occur within the detection zone 7. In order to reduce or eliminate the risk of overfill, the sloping surface might then assist in permitting a surplus of blood to flow away from the separation zone area.

FIG. 11B is a cross-sectional view similar to the view in FIG. 11A, but with the pre-filter removed.

FIG. 11C is a cross-sectional view similar to the view in FIG. 11B, but wherein also the separation filter is removed, hence only illustrating the detection filter 7 as arranged in the recess 33 in the bottom support plane 32 of the housing inner, bottom, part 3B.

It should be clear that the invention is not limited to the illustrated embodiments, but that it can be varied in a number of ways within the scope of the appended claims.

The invention claimed is:

1. An arrangement for collection and separation of a body fluid for purposes of analysis of at least one component of a sample of the body fluid, comprising
    means for receiving a body fluid,
    a filter arrangement comprising
        a separation filter arrangement comprising one or more separation filters for separation of the component or components to be analyzed and
        a detection zone in or in connection to the separation filter arrangement,
    wherein the filter arrangement comprises
        a pre-filter having a filter volume adapted to be capable to receive a volume of body fluid exceeding a volume of a sample to be analyzed, that the pre-filter comprises
            a first portion defining a sample zone volume arranged to form a sample zone and
            at least one second portion defining an excess fluid removal zone volume and being adapted to form at least one excess fluid removal zone, said at least one excess fluid removal zone being spatially separate from said sample zone and the excess removal zone volume exceeding said sample zone volume, that the separation filter arrangement is arranged in communication with the sample zone and defines a separation zone volume forming a separation zone, and in that flow control means are provided to control transportation or flow of body fluid to the excess fluid to the at least one excess fluid removal zone and/or to the separation filter arrangement forming the separation zone and to the at least one excess fluid removal zone;

wherein the flow control means are adapted to control the transportation or flow of body fluid by controlling, at least indirectly, at least a speed of transportation or flow of body fluid in a first separation phase wherein received body fluid is transported at a first speed from the sample zone and separated into the at least one component to be analyzed in the separation zone until the separation zone is substantially filled and in a second excess removal phase, the transportation or flow speed, and initiation of transportation or flow, of excess body fluid from the sample zone to the at least one excess removal zone comprising a second speed, said first speed being higher than the second speed, the total excess removal zone volume being at least twice said sample zone volume;

wherein the flow control means are adapted to control the transportation or flow of body fluid by dividing the flow or transportation into the first, initial, separation phase along a first path of the pre-filter and into the second, excess removal, phase along a second path of the pre-filter, said two phases being sequential and separated in time and space, and in that, in the first separation phase, the first portion of the pre-filter is adapted to allow a plasma transport from the sample zone at the first speed to fill the separation zone volume with plasma such that the plasma will be collected at an end of the flow path to the separation zone volume, and in that in the second, excess removal, phase, the larger excess removal zone volume provides for a transportation at the second speed for removal of excess body fluid from the sample zone and storing of excess body fluid in said excess removal zone volume;

said arrangement configured such that said at least one excess removal zone does not overlap said sample zone.

2. An arrangement according to claim 1, wherein the separation zone volume defined by the separation filter arrangement is smaller than the sample zone volume.

3. An arrangement according to claim 1, wherein the flow control means comprise mechanical means adapted to exert a mechanical pressure on the pre-filter at, or defining, borders between the sample zone and the excess removal zone/zones, whereby the amount of exerted pressure controls speed of the flow, a high pressure providing a slower transport or flow and a lower pressure resulting in a faster transport or flow.

4. An arrangement according to claim 3, wherein the flow control means are formed by walls defining a sample chamber comprising the sample zone.

5. An arrangement according to claim 4, wherein the walls defining the sample chamber are so formed or arranged that air is allowed to escape.

6. An arrangement according to claim 1, wherein the flow control means comprise a barrier formed between the sample zone and at least the excess removal zone or zones, said barrier comprising a hydrophobic coating allowing to, in a controllable manner, control the transport to at least the excess removal zone or zones.

7. An arrangement according to claim 1, wherein the flow control means comprise a barrier formed between the sample zone and at least the excess removal zone or zones, said barrier being formed by a narrow pre-filter passage.

8. An arrangement according to claim 1, wherein the pre-filter comprises a first portion with the flow control means forming the sample zone and two on opposite sides symmetrically disposed second portions each forming a flow excess removal zone.

9. An arrangement according to claim 8, wherein the two on opposite sides symmetrically disposed second portions each forming a flow excess removal zone, each have an outwardly, away from the first portion forming the sample zone, flaring shape, assisting in providing an acceleration transportation of excess fluid from the sample zone.

10. An arrangement according to claim 1, wherein the pre-filter comprises a first portion forming the sample zone and on one side thereof a second portion forming a flow excess removal zone, said second portion forming a flow excess removal zone flaring outwardly from the first portion.

11. An arrangement according to claim 1, wherein the separation filter arrangement is disposed adjacent and in communication with the first portion, but at least partly in a different plane than said first portion, on a different side thereof that a side or sides at which the at least one second portion is located.

12. An arrangement according to claim 1, wherein the pre-filter is made of a porous, hydrophilic material.

13. An arrangement according to claim 1, wherein the at least one excess removal zone is adapted to receive a body fluid volume being between 1.5-10 times the sample zone volume.

14. An arrangement according to claim 1, wherein the filter arrangement is disposed on a bottom support plane of an arrangement housing bottom portion, said plane being arranged in a horizontal or in a sloping manner, with the pre-filter on top, the separation filter arrangement below the pre-filter, and the detection zone below, or adjacent, the separation filter arrangement, either comprising a separate detection filter or comprising a detection zone of the separation filter arrangement, and in that a detection window is provided in the bottom support plane or in a cover or label means covering at least part of a bottom of the bottom support plane allowing for visual inspection of the selected at least one component of the body fluid sample collected in the detection zone allowing establishment of the existence of haemolysis.

15. A method for collection and separation of a body fluid for purposes of analysis of at least one component of a sample of the body fluid, comprising the step of:

providing a sample of a body fluid to an arrangement comprising a filter arrangement comprising a separation arrangement comprising one or more separation filters for separation of the component or components to be analyzed and a detection zone comprising a detection filter arranged in connection to the separation arrangement or formed by a section of the separation arrangement, wherein the body fluid providing step comprises providing a larger amount of body fluid to a pre-filter of the filter arrangement than the amount or volume intended to be used for the analysis, and in that the method further comprises the steps of:

performing an initial separation by, via a first portion of the pre-filter forming a sample zone volume forming a sample zone allowing the body fluid to flow to a separation zone defined by a separation arrangement comprising one or more separation filters arranged in communication with the sample zone until the separation filter arrangement is substantially filled with the selected at least one component to be analyzed;

removing excess body fluid provided to the sample zone formed by the first portion of the pre-filter by allowing said excess body fluid to flow or be transported to at least one excess removal zone formed by at least one second portion of the pre-filter, the volume of said at least one excess removal zone exceeding the volume of said sample zone; the method comprising controlling the transportation or the flow at least to the at least one excess removal zone by means of flow control means, wherein the flow control means are adapted to control the transportation or flow of body fluid by controlling, at least indirectly, at least the speed of transportation or flow of body fluid in a first separation phase wherein received body fluid is transported at a first speed from the sample zone and separated into the at least one component to be analyzed in the separation zone until the separation zone is substantially filled, and, in a second excess removal phase, the transportation or flow speed, and initiation of transportation or flow, of excess body fluid from the sample zone to the at least one excess removal zone comprising a second speed, said first speed being higher than the second speed, the total excess removal zone volume being at least twice said sample zone volume and wherein the flow control means are adapted to control the transportation or flow of body fluid by dividing the flow or transportation into the first, initial, separation phase along a first path of the pre-filter into the second, excess removal, phase along a second path of the pre-filter, said two phases being sequential and separated in time and space, and in that, in the first separation phase, the first portion of the pre-filter is adapted to allow a plasma transport from the sample zone at the first speed to fill the separation zone volume with plasma such that the plasma will be collected at an end of the flow path to the separation zone volume, and in that in the second, excess removal, phase, the larger excess removal zone volume provides for a transportation at the second speed for removal of excess body fluid from the sample one and storing of excess body in said excess removal zone volume; said arrangement configured such that said at least one excess removal zone does not overlap said sample zone.

16. An arrangement according to claim 5, wherein the walls defining the sample chamber comprise two or three walls.

17. An arrangement according to claim 5, wherein the walls defining the sample chamber comprises an opening in at least one wall.

* * * * *